United States Patent [19]

Bloom

[11] 3,971,371

[45] July 27, 1976

[54] URINE-SENSING PAD

[76] Inventor: Stanley Bloom, 1048 Kenyon Ave., Plainfield, N.J. 07060

[22] Filed: May 27, 1975

[21] Appl. No.: 580,776

[52] U.S. Cl............................................ 128/138 A
[51] Int. Cl.² .......................................... A61B 19/00
[58] Field of Search ............ 128/138 A, 138 R, 2 R, 128/2.1 R; 200/61.04

[56] References Cited
UNITED STATES PATENTS

| 1,285,986 | 11/1918 | Grafford | 128/138 A |
| 2,127,538 | 8/1938 | Seiger | 128/138 A |
| 2,687,721 | 8/1954 | Ellison | 128/138 A |
| 3,245,068 | 4/1966 | Wegryn et al. | 128/138 A |

Primary Examiner—Lawrence W. Trapp

[57] ABSTRACT

The pad comprises a sheet of flexible insulating material carrying an array of conductive sensor strips on one surface. On the opposite surface of the insulating sheet are provided four conductive pickup strips, two at each end. One pickup strip at each end is connected through the sheet by metallic staples to the odd-numbered sensor strips, and the other two pickup strips are connected by staples to the even-numbered sensor strips. Thus, two sets of sensor strips are provided, and two connections are made to each strip in each set, and these connections are used to couple the pad into an alarm circuit.

In a second arrangement, conductive tapes are used to connect together sensor strips and pickup strips.

In use, the moisture being sensed makes an electrical connection between the two sets of sensing strips, thus activating the alarm circuit.

5 Claims, 6 Drawing Figures

URINE-SENSING PAD

BACKGROUND OF THE INVENTION

Many pads are available for sensing the presence of urine in a bedwetting detection and training system. However, none of these known pads is as simple in construction and as long lasting as that described herein. Urine-detecting pads in general operate on the principle that the urine (which is suitably electrically conductive) completes an electical circuit between two sets of sensing elements, each set being connected in series with an external alarm system. The completion of the pad circuit by the urine activates the alarm, which wakes the patient. Repeated awakenings by this process train the patient by the conditioned-reflex method.

Some urine-sensing pads in the prior art utilize thin strips of conductive ribbon or the like, as sensor elements, secured to an insulating pad. These sensor elements or strips can be laid down on the pad, either by continuous rolls of adhesive-backed metal striping onto continuous rolls of insulating flexible substrate, out of which pad-size sections are subsequently cut, or by finite-length metal strips laid onto pre-cut pad-size substrates. In any case, the more difficult and time consuming manufacturing operation concerns the subsequent steps of making a common electrical connection to the elements of each of the two sets. The invention described herein achieves this connection in a much simpler, and less expensive, manner than in any known pad. Also, by virtue of its method of construction, the present pad is more long-lasting than others.

SUMMARY OF THE INVENTION

Briefly, the invention comprises an insulating pad having first and second groups of conductive strips formed on a surface thereof, with each group having at least two common pickup strips for electrically connecting together all of the strips of the group. Novel means are provided for making the various interconnections required.

DESCRIPTION OF THE PREFERRED EMBODIMENTS

Figure 1:
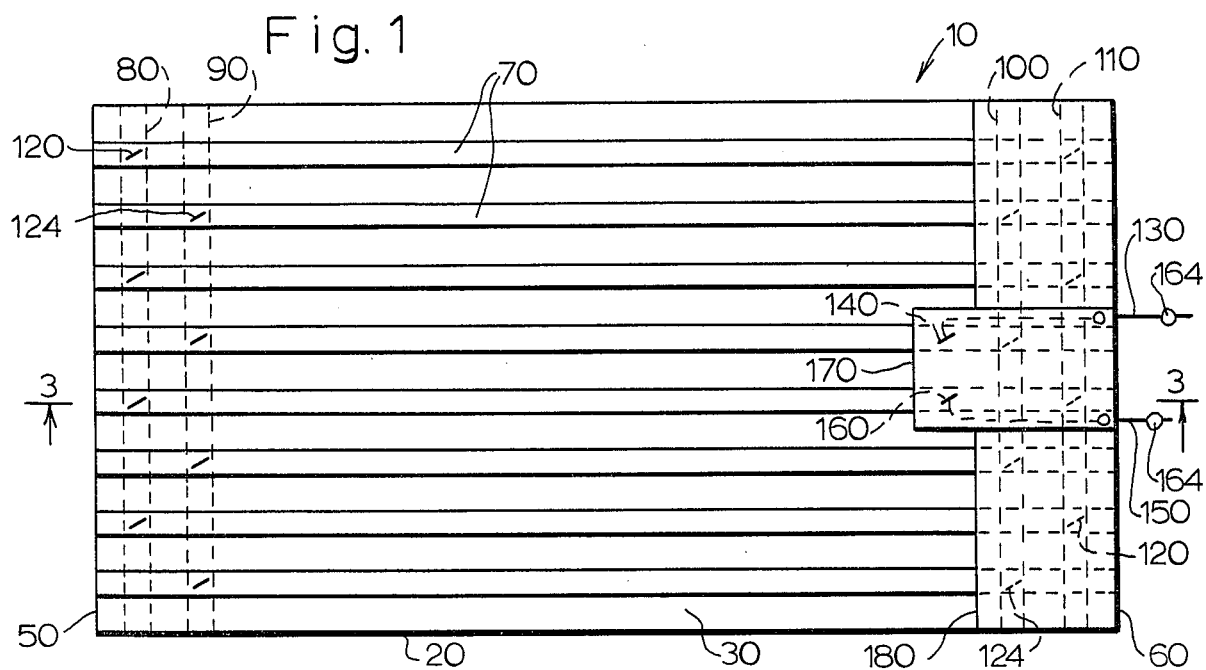
FIG. 1 is a plan view of a pad embodying the invention.
Figure 2:
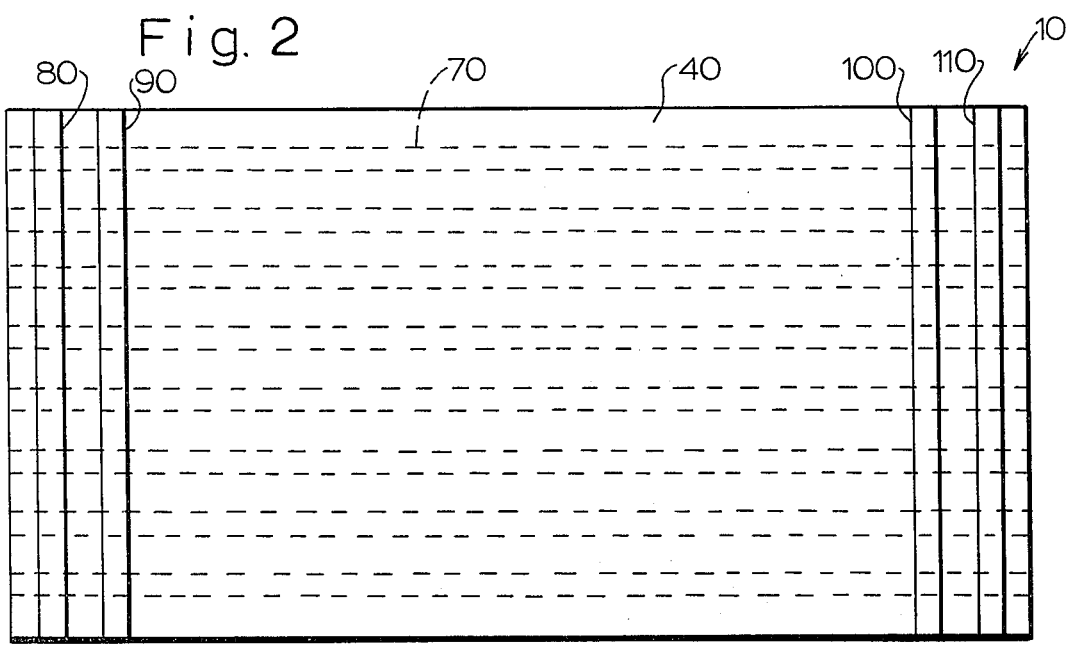
FIG. 2 is a view of the bottom surface of the pad of FIG. 1.
Figure 3:
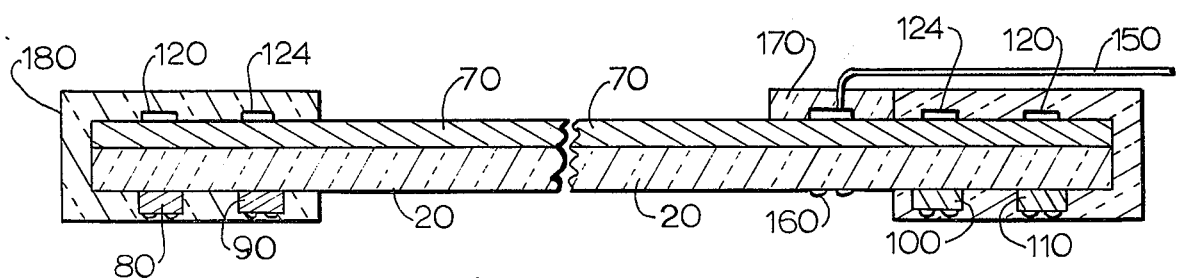
FIG. 3 is a sectional view along the lines 3—3 in FIG. 1.

A urine-sensing pad 10 embodying the invention comprises a sheet 20 of a flexible, non-stretchable insulating material, such as Mylar, having a top surface 30, a bottom surface 40, a left end 50, and a right end 60. A plurality of parallel conductive sensor strips 70, of aluminum or the like, are bonded to the top surface 30 of the sheet 20, suitably spaced apart from each other. On the opposite surface 40 of the sheet are provided two similar conductive pickup strips 80 and 90, of aluminum or the like, at the left end of the sheet, and two pickup strips 100 and 110 are provided at the right end of the sheet, all of the pickup strips being oriented at substantially 90° to the sensor strips on the top surface.

Pickup strips 80 and 110 are electrically connected to the odd-numbered sensor strips 70 on the top surface 30 of sheet 20 by means of a staple-like conductive member 120, which, in actual practice, is a staple which is set in place by a conventional stapling machine. Similarly, pickup strips 90 and 100 are connected to the even-numbered sensor strips by staples 124. The conductive staples make a firm electrical connection between the sensor strips on the top surface and the pickup strips on the bottom surface. Thus, the sensor strips are connected in two sets electrically, and, to connect the sets to external circuitry, an insulated lead wire 130 is connected by a staple 140 to an even-numbered sensor strip, and an insulated wire 150 is connected by a staple 160 to an odd-numbered strip. The wires 130 and 150 are provided with suitable terminals 164, by means of which the sets of sensor strips can be connected to an electrical alarm circuit. In the completed pad, a small strip of insulating tape 170 is provided over the staples 140 and 160 and the bare portions of wires 130 and 150. Similarly strips 180 of protective tape may be provided covering the pickup strips at one or both ends of the pad 10.

If desired, the lead wires 130 and 150 can be secured to the pad by drawing them through a hole in the pad and then knotting the wires (not shown).

Figure 4:
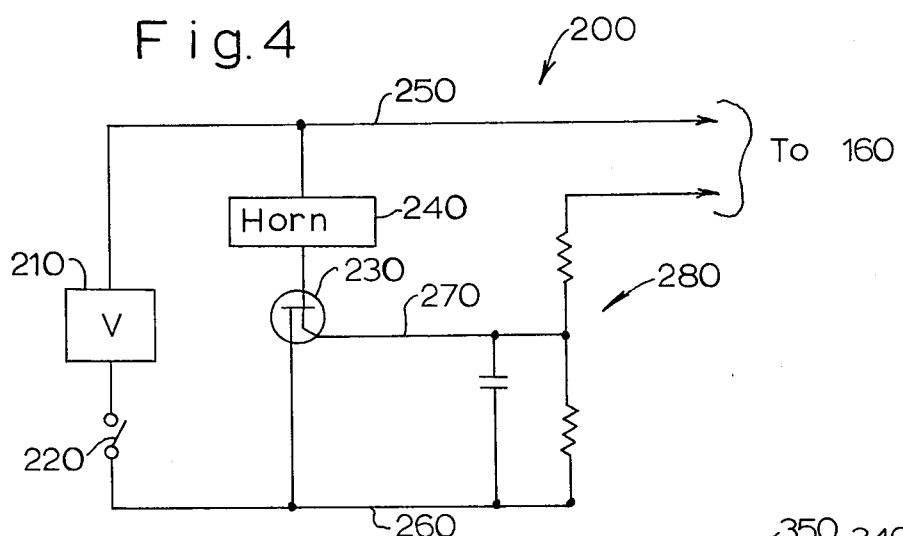
FIG. 4 is a schematic representation of a circuit in which the pad of the invention may be operated.

A typical circuit 200 for operating the urine-sensing pad 10 is shown in FIG. 4 and includes a series-connected power source 210, such as a battery, and normally-closed switch 220 in parallel with a series-connected silicon-controlled rectifier (SCR) 230 and alarm element 240 such as a horn, both series circuits being connected between buses 250 and 260. The output electrode or collector of SCR 230 is connected by a lead 270 to a suitable point on a voltage divider 280. A capacitor is connected across a portion of the voltage divider from lead 270 to bus 260. Bus 250 and the free end of the voltage divider are connected to terminals 164, to which the urine-sensing pad is connected.

In operation of circuit 200, urine present on pad 10 between odd and even strips 70 completes the electrical circuit, activates the SCR, and causes battery current to flow through the horn 240 which provides the desired alarm.

Figure 5:
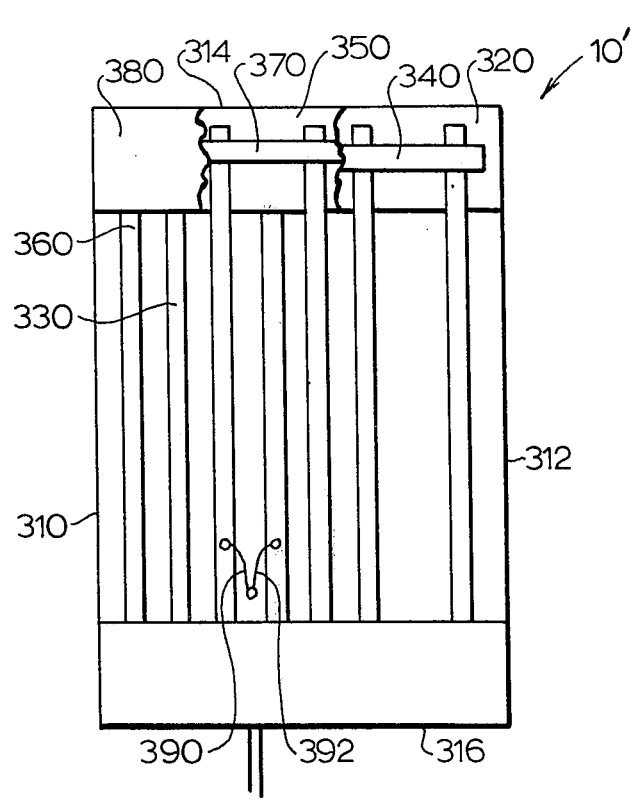
FIG. 5 is a plan view of a modification of the invention.
Figure 6:
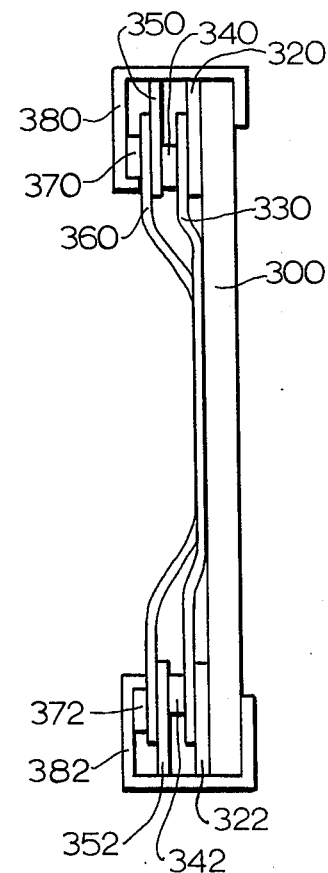
FIG. 6 is a side view of the apparatus of FIG. 5.

A pad 10' embodying a modification of the invention, shown in FIGS. 5 and 6, comprises an insulating sheet 300, of Mylar or the like, having left and right edges, 310 and 312, and upper and lower edges, 314 and 316. Strips 320 and 322, of a double-faced adhesive, which is well known in the art, are secured to the top surface of sheet 300 along the upper and lower edges thereof. A set of parallel conductive sensor strips, denoted "even" strips and made of aluminum, for example, are secured to the top surface of sheet 300 and extending from the upper to the lower edge thereof. The strips may be secured in place, for example, by means of an adhesive backing and by the adhesive of strips 320 and 322. Even pickup strips 340 and 342, for the even sensor strips, are placed across and in electrical contact with sensor strips 330 at the upper and lower ends thereof, and held in place by the adhesive strips 320 and 322. An insulating strip 350 and 352 of double-faced adhesive masking tape or the like is placed over the pickup strips 340 and 342.

A set of parallel, conductive sensor strips 360 denoted "odd" strips is now secured to the sheet 300, extending between the upper and lower edges thereof and with each odd strip 360 alternating with an even strip 330. These strips 360 are also held in place by an adhesive backing or the like and by adhesive strips 350 and 352. Odd pickup strips 370 and 372 are placed over the odd sensor strips 360, in electrical contact therewith, at the upper and lower edges of the sheet and secured in place by the strips of masking tape 350 and 352. A final protective strip 380, 382 of plastic or the like is provided over the upper and lower ends of the sheet covering the odd pickup strips 370 and 372. Connecting wires 390 and 392 are secured, one to an odd and one to an even sensor strip, to complete the assembly and to provide means for making connection to an external circuit.

It is important to note that each member of the even and odd sets of sensor strips in pads 10 and 10' is connected to two pickup strips; thus, there are two pickup strips at each end of the pad. By this simple means, the life of the entire sensor pad is at least doubled. Urine-sensing pads in general are subject to flexing and to chemical corrosion during use, and this, in time, may cause breaks to occur in various sensor strips. If only one pickup strip is provided for the odd, and one for the even, set of sensor strips, then such a break would make the broken sensor strip inoperative over the distance between the break and the unconnected end of that strip. However, by providing, as described, a second pickup strip at each end of the pad, one break in a sensor strip does not render that strip inoperative. A sensor strip with one break now suffers no degradation whatever, and even a strip with multiple breaks remains operative over the portions of its length from the pickup strips to the first breaks.

What is claimed is:

1. A pad for electrically detecting the presence of a conductive fluid comprising
   a sheet of insulating material having top and bottom surfaces and first and second ends,
   a plurality of parallel fluid-sensing strips of conductive material on the top surface of said sheet including first, second . . . n strips,
   a first connecting strip connected to the odd-numbered fluid-sensing strips which are thus connected in a common first set,
   a second connecting strip connected to the even-numbered fluid-sensing strips which are thus connected in a common second set,
   said first and second connecting strips being on the bottom surface of said sheet, and
   metal staples making the connections between the fluid-sensing strips and their connecting strips through said sheet.

2. The pad defined in claim 1 wherein said first conductive strips are odd-numbered and said second conductive strips are even-numbered and including a first external lead secured to one odd-numbered conductive strip and a second external lead secured to one even-numbered conductive strip whereby said odd-numbered and even-numbered strips can be connected in an electrical circuit.

3. A pad for electrically detecting the presence of a conductive fluid comprising
   a sheet of insulating material having top and bottom surfaces and first and second ends,
   a plurality of parallel urine-sensing strips of conductive material on the top surface of said sheet including first, second . . . n strips, there thus being even-numbered and odd-numbered urine-sensing strips,
   first and second connecting strips on the bottom surface of said sheet adjacent to said first end,
   third and fourth connecting strips on the bottom surface of said sheet adjacent to said second end,
   metal staples making connections through said sheet between said first and third connecting strips and the odd-numbered urine-sensing strips and metal staples making connections through said sheet between said second and fourth connecting strips and the even-numbered urine-sensing strips.

4. A pad for electrically detecting the presence of a conductive fluid comprising
   a sheet of insulating material having top and bottom surfaces and first and second ends and a long axis,
   first and second layers of adhesive material on said top surface of said sheet at said first and second ends, respectively,
   a plurality of first parallel strips disposed on said top surface of said sheet parallel to said long axis, said first strips having first and second opposite ends, the first ends being secured to said first layer of adhesive material and said second ends being secured to said second layer of adhesive material,
   a first common cross conductor secured to said first ends of said first conductive strips on said first layer of adhesive material and a second common cross conductor secured to said second ends of said first conductive strips on said second layer of adhesive material,
   third and fourth layers of adhesive material on said sheet at said first and second ends, respectively, and overlying said first and second layers of adhesive material and the first and second ends of said first conductive strips and said first and second common cross conductors,
   a plurality of second parallel strips disposed on said top surface of said sheet and parallel to said long axis, said strips being interleaved with said first conductive strips but spaced and insulated therefrom, said second strips having first and second opposite ends, the first ends being secured to said third layer of adhesive material and said second ends being secured to said fourth layer of adhesive material,
   a third common cross conductor secured to said first ends of said second conductive strips on said third layer of adhesive material and a fourth common cross conductor secured to said second ends of said second conductive strips on said fourth layer of adhesive material, and
   an insulating cover layer covering said first and second ends of said sheet and all of the elements supported thereon.

5. The pad defined in claim 4 and including a first external lead secured to one first conductive strip and a second external lead secured to one second conductive strip whereby said first and second conductive strips can be connected in an electrical circuit.